(12) United States Patent
Boye et al.

(10) Patent No.: US 12,064,225 B2
(45) Date of Patent: *Aug. 20, 2024

(54) PRESSURE SENSOR AND GUIDE WIRE WITH HYDROPHILIC MATERIAL

(71) Applicant: ST. JUDE MEDICAL COORDINATION CENTER BVBA, Zaventem (BE)

(72) Inventors: Shawn Boye, Menlo Park, CA (US); Fredrik Mahlin, Uppsala (SE); Stefan Tiensuu, Uppsala (SE); Niklas Borg, Storvreta (SE); Johan Mattsson, Uppsala (SE); Johan Grundin, Alunda (SE); Mats Hilmersson, Bromma (SE); Sara Sundler, Uppsala (SE); Dean Hacker, Maple Grove, MN (US); Ryan Cerepak, Champlin, MN (US)

(73) Assignee: ST. JUDE MEDICAL COORDINATION CENTER BVBA, Zaventem (BE)

( * ) Notice: Subject to any disclaimer, the term of this patent is extended or adjusted under 35 U.S.C. 154(b) by 602 days.

This patent is subject to a terminal disclaimer.

(21) Appl. No.: 17/124,864

(22) Filed: Dec. 17, 2020

(65) Prior Publication Data

US 2021/0169358 A1 Jun. 10, 2021

Related U.S. Application Data

(63) Continuation of application No. 15/053,308, filed on Feb. 25, 2016, now Pat. No. 10,898,090.
(Continued)

(51) Int. Cl.
*A61M 25/00* (2006.01)
*A61B 5/00* (2006.01)
(Continued)

(52) U.S. Cl.
CPC .............. *A61B 5/036* (2013.01); *A61B 5/021* (2013.01); *A61B 5/0215* (2013.01);
(Continued)

(58) Field of Classification Search
CPC ....... A61B 5/036; A61B 5/021; A61B 5/0215; A61B 5/6851; A61B 2562/0247;
(Continued)

(56) References Cited

U.S. PATENT DOCUMENTS 3,521,620 A 7/1970 Cook
4,456,013 A 6/1984 De Rossi et al.
(Continued)

FOREIGN PATENT DOCUMENTS

DE 24 20 610 A1 10/1975
EP 0 387 453 A1 9/1990
(Continued)

OTHER PUBLICATIONS

"In", The American Heritage Dictionary of the English Language, Fifth Edition (2014)Houghton Mifflin Harcourt Publishing Company, pp. 1-3, Retrieved from <https://ahdictionary.co/word/search.html?q-IN> on Mar. 25, 2015.
(Continued)

*Primary Examiner* — David J. McCrosky
(74) *Attorney, Agent, or Firm* — Foley & Lardner LLP

(57) ABSTRACT

A pressure sensor configured for biological pressure measurement at a distal end portion of an elongated member comprises a dissolvable hydrophilic material coated on a surface of the pressure sensor. A guide wire for biological pressure measurement may include a tube extending along a longitudinal axis of the guide wire; and a pressure sensor for biological pressure measurement, at least a portion of the pressure sensor being mounted within the tube. The pressure sensor comprises a pressure sensor membrane facing a top
(Continued)

side of the tube. A circumferential wall of the tube includes at least six openings: a first distal opening, a second distal opening located on a right side of the tube, a third distal opening located on a left side of the tube, a first proximal opening, a second proximal opening located on a right side of the tube, and a third proximal opening located on a left side of the tube. The first distal opening is larger than the second and third distal openings, and the first proximal opening is larger than the second and third proximal openings.

8 Claims, 13 Drawing Sheets

Related U.S. Application Data

(60) Provisional application No. 62/121,243, filed on Feb. 26, 2015.

(51) Int. Cl.
  *A61B 5/021* (2006.01)
  *A61B 5/0215* (2006.01)
  *A61B 5/03* (2006.01)

(52) U.S. Cl.
  CPC .... *A61B 5/6851* (2013.01); *A61B 2562/0247* (2013.01); *A61B 2562/17* (2017.08); *A61M 2025/0002* (2013.01); *A61M 2025/0003* (2013.01)

(58) Field of Classification Search
  CPC ...... A61B 2562/17; A61M 2025/0002; A61M 2025/0003
  See application file for complete search history.

(56) References Cited

U.S. PATENT DOCUMENTS

| | | | |
|---|---|---|---|
| 4,534,355 A * | 8/1985 | Potter | A61B 5/14542 600/360 |
| 4,712,566 A | 12/1987 | Hok | |
| 4,941,473 A | 7/1990 | Tenerz et al. | |
| 4,955,895 A | 9/1990 | Sugiyama et al. | |
| 5,018,529 A | 5/1991 | Tenerz et al. | |
| 5,085,223 A | 2/1992 | Lars et al. | |
| 5,091,800 A * | 2/1992 | Offenbacher | G01N 21/6428 250/462.1 |
| 5,097,841 A | 3/1992 | Moriuchi et al. | |
| 5,120,420 A * | 6/1992 | Nankai | C12Q 1/004 435/817 |
| 5,125,058 A | 6/1992 | Tenerz et al. | |
| 5,437,288 A | 8/1995 | Schwartz et al. | |
| 5,549,109 A | 8/1996 | Samson et al. | |
| RE35,648 E | 11/1997 | Tenerz et al. | |
| 5,993,378 A | 11/1999 | Lemelson | |
| 6,019,728 A | 2/2000 | Iwata et al. | |
| 6,045,734 A | 4/2000 | Luther et al. | |
| 6,162,182 A | 12/2000 | Cole | |
| 6,167,763 B1 | 1/2001 | Tenerz et al. | |
| 6,248,083 B1 | 6/2001 | Smith et al. | |
| 6,295,990 B1 | 10/2001 | Lewis et al. | |
| 6,343,541 B1 | 2/2002 | Smith | |
| 6,491,712 B1 | 12/2002 | O'Connor | |
| 7,011,636 B2 | 3/2006 | Tenerz | |
| 7,222,539 B2 | 5/2007 | Tulkki | |
| RE39,863 E | 10/2007 | Smith | |
| 7,724,148 B2 | 5/2010 | Samuelsson et al. | |
| 8,174,395 B2 | 5/2012 | Samuelsson et al. | |
| 8,461,997 B2 | 6/2013 | Samuelsson et al. | |
| 8,551,022 B2 | 10/2013 | Von Malmborg | |
| 9,144,664 B2 | 9/2015 | Jacobsen et al. | |
| 10,426,404 B2 | 10/2019 | Hilmersson | |
| 10,898,090 B2 * | 1/2021 | Boye | A61B 5/0215 |
| 11,547,359 B2 | 1/2023 | Hilmersson | |
| 2002/0013540 A1 | 1/2002 | Jacobsen et al. | |
| 2002/0049392 A1 | 4/2002 | Demello | |
| 2002/0077520 A1 | 6/2002 | Segal et al. | |
| 2002/0173785 A1 | 11/2002 | Spear et al. | |
| 2003/0009208 A1 | 1/2003 | Snyder et al. | |
| 2003/0069522 A1 | 4/2003 | Jacobsen et al. | |
| 2005/0004515 A1 | 1/2005 | Hart et al. | |
| 2005/0038359 A1 | 2/2005 | Aimi et al. | |
| 2005/0043670 A1 | 2/2005 | Rosenberg | |
| 2005/0187487 A1 | 8/2005 | Azizkhan et al. | |
| 2005/0268725 A1 | 12/2005 | Tulkki | |
| 2006/0004346 A1 | 1/2006 | Begg | |
| 2006/0211946 A1 | 9/2006 | Mauge et al. | |
| 2007/0088220 A1 | 4/2007 | Stahmann | |
| 2007/0157588 A1 | 7/2007 | Dauber et al. | |
| 2008/0045986 A1 | 2/2008 | To et al. | |
| 2008/0200770 A1 | 8/2008 | Hubinette | |
| 2009/0020961 A1 | 1/2009 | Kameyama et al. | |
| 2009/0062602 A1 | 3/2009 | Rosenberg et al. | |
| 2009/0177185 A1 | 7/2009 | Northrop | |
| 2009/0192412 A1 | 7/2009 | Sela et al. | |
| 2009/0318798 A1 | 12/2009 | Singh et al. | |
| 2010/0063479 A1 | 3/2010 | Merdan et al. | |
| 2010/0145308 A1 | 6/2010 | Layman et al. | |
| 2010/0152663 A1 | 6/2010 | Darr | |
| 2010/0217304 A1 | 8/2010 | Angel et al. | |
| 2010/0228112 A1 | 9/2010 | Von Malmborg | |
| 2010/0262041 A1 | 10/2010 | Von Malmborg | |
| 2011/0004198 A1 | 1/2011 | Hoch | |
| 2011/0137186 A1 | 6/2011 | Limacher et al. | |
| 2011/0160648 A1 | 6/2011 | Hoey | |
| 2011/0160680 A1 | 6/2011 | Cage et al. | |
| 2011/0213220 A1 | 9/2011 | Samuelsson et al. | |
| 2011/0245808 A1 | 10/2011 | Voeller et al. | |
| 2012/0289808 A1 | 11/2012 | Hubinette | |
| 2013/0102927 A1 | 4/2013 | Hilmersson | |
| 2013/0102928 A1 | 4/2013 | Sotos et al. | |
| 2013/0274618 A1 | 10/2013 | Hou et al. | |
| 2013/0296718 A1 | 11/2013 | Ranganathan et al. | |
| 2014/0004253 A1 * | 1/2014 | Ruane | A61M 25/1029 427/2.24 |
| 2014/0058338 A1 | 2/2014 | Adams et al. | |
| 2014/0180066 A1 | 6/2014 | Stigall | |
| 2015/0032011 A1 | 1/2015 | McGowan et al. | |
| 2015/0173629 A1 | 6/2015 | Corl et al. | |
| 2016/0249821 A1 | 9/2016 | Boye et al. | |
| 2016/0262698 A1 | 9/2016 | Mahlin | |
| 2019/0313922 A1 | 10/2019 | Ness et al. | |
| 2019/0380652 A1 | 12/2019 | Hilmersson | |

FOREIGN PATENT DOCUMENTS

| | | |
|---|---|---|
| EP | 5 225 67 B1 | 10/1996 |
| EP | 0 521 595 B1 | 5/1999 |
| EP | 1 340 516 A1 | 9/2003 |
| EP | 0 877 574 B1 | 10/2003 |
| EP | 1 849 409 A1 | 10/2007 |
| EP | 2 085 108 A2 | 8/2009 |
| EP | 1 545 680 B1 | 9/2010 |
| JP | 63-158064 A | 7/1988 |
| JP | 05-184666 A | 7/1993 |
| JP | 07-326770 A | 12/1995 |
| JP | H11-508160 A | 7/1999 |
| JP | 2005-046603 A | 2/2005 |
| JP | 2009-172385 A | 8/2009 |
| JP | 2009-529750 A | 8/2009 |
| JP | 2011-529750 A | 12/2011 |
| JP | 2014-042645 A | 3/2014 |
| JP | 2015-501184 A | 1/2015 |
| SE | 441725 B | 11/1985 |
| SE | 453561 B | 2/1988 |
| SE | 454045 B | 3/1988 |
| SE | 460396 B | 10/1989 |
| SE | 469454 B | 7/1993 |
| SE | 0877574 T3 | 10/2003 |
| WO | WO-97/00641 A1 | 1/1997 |
| WO | WO-00/69323 A2 | 11/2000 |

(56) References Cited

FOREIGN PATENT DOCUMENTS

| WO | WO-03/094693 | A2 | 11/2003 |
|----|----|----|----|
| WO | WO-2004/011076 | A2 | 2/2004 |
| WO | WO-20077050718 | A1 | 5/2007 |
| WO | WO-2009/020954 | A1 | 2/2009 |
| WO | WO-2009/029639 | A1 | 3/2009 |
| WO | WO-2009/054803 | A1 | 4/2009 |
| WO | WO-2009/112060 | A1 | 9/2009 |
| WO | WO-2011/041720 | A2 | 4/2011 |
| WO | WO-2011/161212 | A1 | 12/2011 |
| WO | WO-2012/000798 | A1 | 1/2012 |
| WO | WO-2014/043704 | A1 | 3/2014 |
| WO | WO-2014/125497 | A1 | 8/2014 |
| WO | WO-2014/149688 | A1 | 9/2014 |
| WO | WO-2016/138226 | A1 | 9/2016 |

OTHER PUBLICATIONS

"-Like". 2011. In The American Heritage Dictionary of the English Language, Boston: Houghton Mifflin. <http://search.credoreference.com/content/entry/hmdictenglang/like/0>.

ASM Int'l, Materials and Coatings for Medical Devices: Cardiovascular. 2009. p. 417-419.

European Intention to Grant, Application No. 16 710 367.0, dated Jan. 23, 2020, 5 pages.

European Office Action, Application No. 18187963.6, dated Nov. 20, 2020, 4 pages.

Extended European Search Report, Application No. 20174470.3, dated Jun. 9, 2020, 8 pages.

Harris et al, New Polyethylene Glycols for Biomedical Applications, Water-Soluble Polymers. ACS Symposium Series; American Chemical Society. 1991. p. 418-429.

International Preliminary Report on Patentability, PCT/IB2013/000903, dated Nov. 13, 2014, 11 pages.

International Preliminary Report on Patentability, PCT/US2016/019498, dated Sep. 8, 2017, 11 pages.

International Preliminary Report on Patentability, PCT/US2019/024292, dated Oct. 29, 2020, 8 pages.

International Search Report and Written Opinion, PCT/US2016/019498, dated Jul. 4, 2016, 17 pages.

International Search Report and Written Opinion, PCT/US2019/024292, dated Jun. 26, 2019, 11 pages.

Japanese Office Action and English translation, Application No. 2017-545550, dated May 14, 2019, 16 pages.

Japanese Office Action and English translation, Application No. JP 2019-237942, dated Oct. 27, 2020, 7 pages.

Kawai, Fusako, Biodegradation of Polyethers (Polyethylene Glycol, Polypropylene Glycol, Polytetramethylene Glycol, and Others,) Biopolymers Online: Biology Chemistry Biotechnology, Applications 9 (2005). Retrieved from <https://onlinelibrary.wiley.com/doi/full/10.1002/3527600035.bpol9012>. (Year: 2005).

Machine translation of JP H07-326770 A.

PCT/ISA/206, International Application No. PCT/US2016/019498, 7 pages.

Radi Medical Systems AB, PressureWire Certus, Brochure, 60680 Rev. 03, Apr. 2008.

tube.Dictionary.com, Dictionary.com Unabridged, Random House, Inc. ,http://dictionary.reference.com/browse/tube> (accessed: Sep. 5, 2014).

USPTO Notice of Allowance, U.S. Appl. No. 15/030,770, dated Jul. 8, 2019, 9 pages.

USPTO Office Action, U.S. Appl. No. 13/804,342, dated Jan. 16, 15, 9 pages.

USPTO Office Action, U.S. Appl. No. 13/804,342, dated Nov. 19, 2015, 12 pages.

USPTO Office Action, U.S. Appl. No. 13/804,342, dated Apr. 7, 2016, 13 pages.

USPTO Office Action, U.S. Appl. No. 13/804,342, dated Sep. 12, 2014, 18 pages.

USPTO Office Action, U.S. Appl. No. 13/806,380, dated Aug. 4, 2017, 15 pages.

Zalipsky et al, Introduction to Chemistry and Biological Applications of Poly(ethylene glycol). ACS Symposium Series; American Chemical Society. 1997. p. 1-13.

USPTO Office Action, U.S. Appl. No. 16/366,112, dated Mar. 30, 2021, 29 pages.

Japanese Office Action, Japanese Application No. 2021-107358, dated Jun. 7, 2022, 14 pages.

Japanese Search Report, Application No. 2021-107358, dated May 25, 2022, 13 pages.

USPTO Notice of Allowance, U.S. Appl. No. 16/551,971, dated May 6, 2022, 6 pages.

USPTO Office Action, U.S. Appl. No. 16/551,971, dated Feb. 15, 2022, 15 pages.

Japanese Search Report, Japanese Application No. 2017-545550, dated Sep. 5, 2018, 15 pages.

USPTO Office Action, U.S. Appl. No. 16/366,112, dated Nov. 2, 2021, 16 pages.

Non-Final Office Action on U.S. Appl. No. 17/736,240 dated Sep. 21, 2023.

Notice of Allowance in U.S. Appl. No. 17/736,240 mailed Jan. 29, 2024.

\* cited by examiner

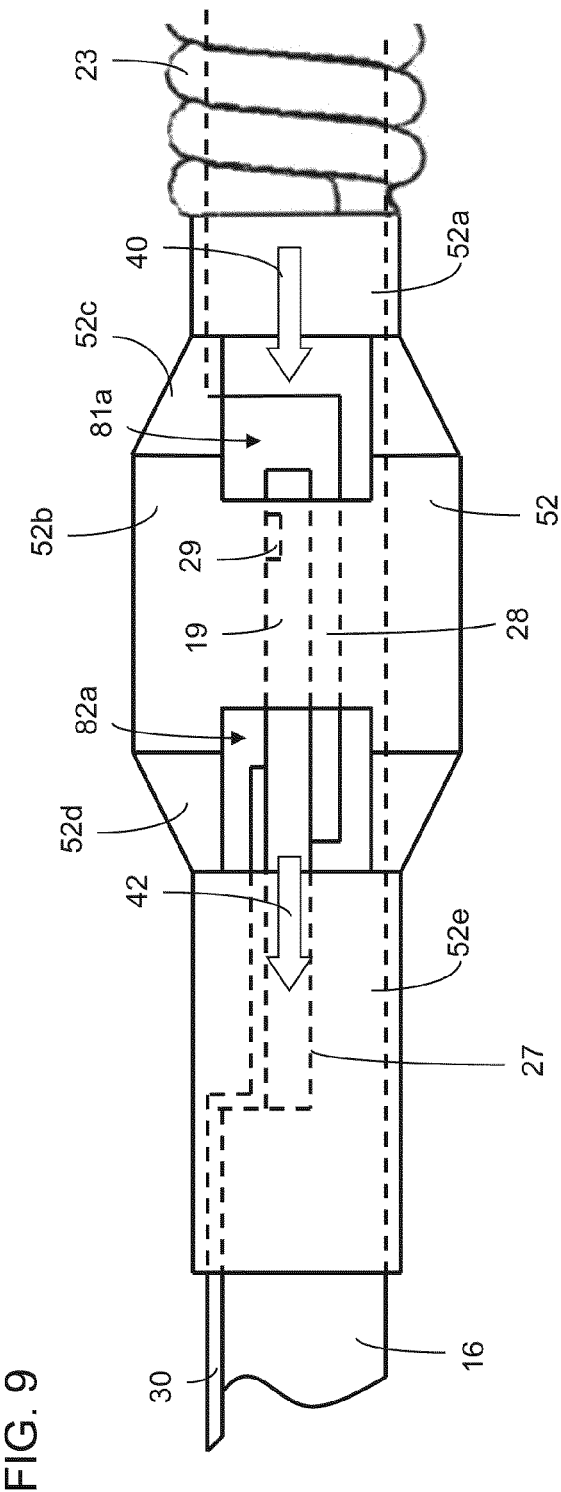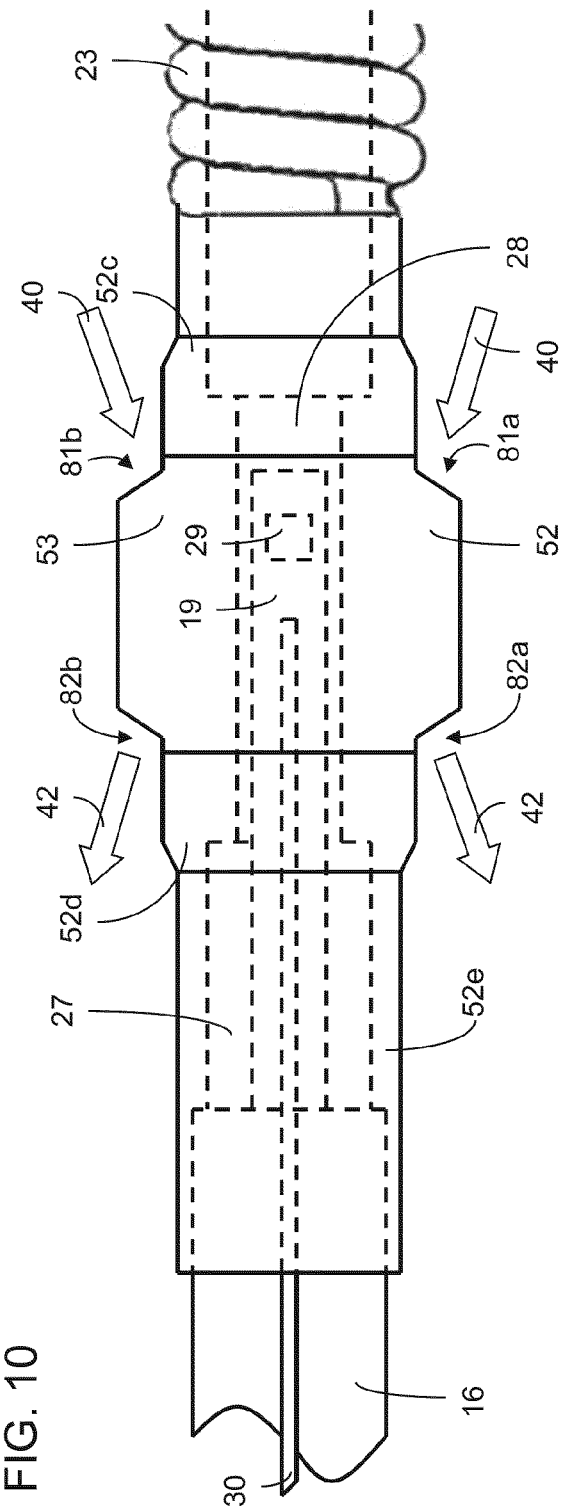

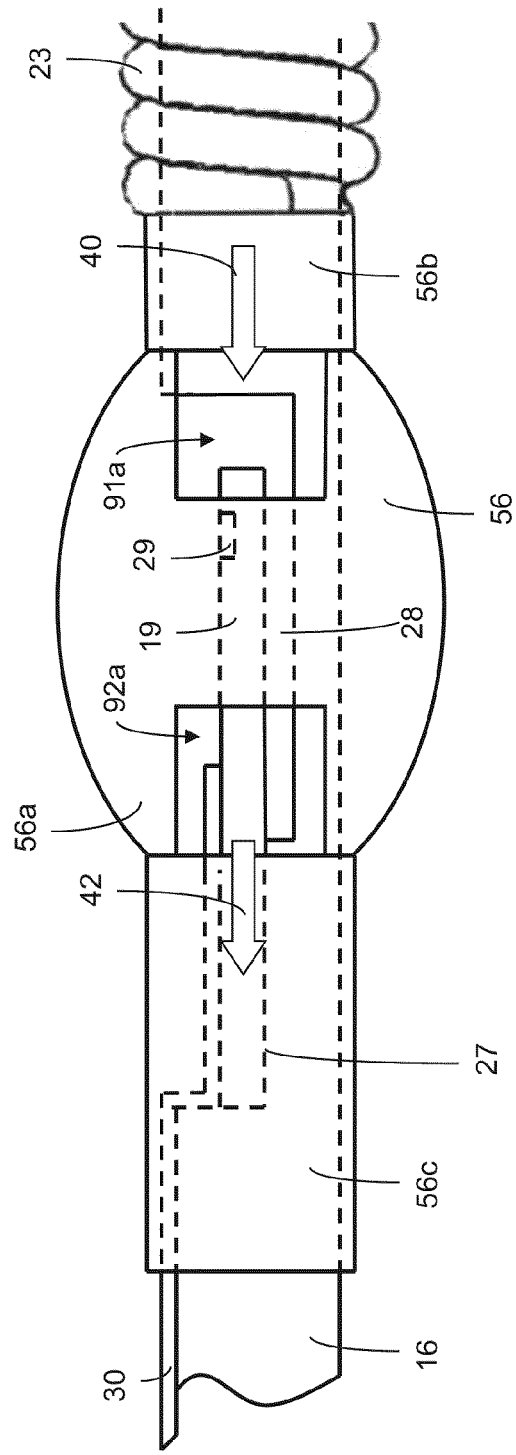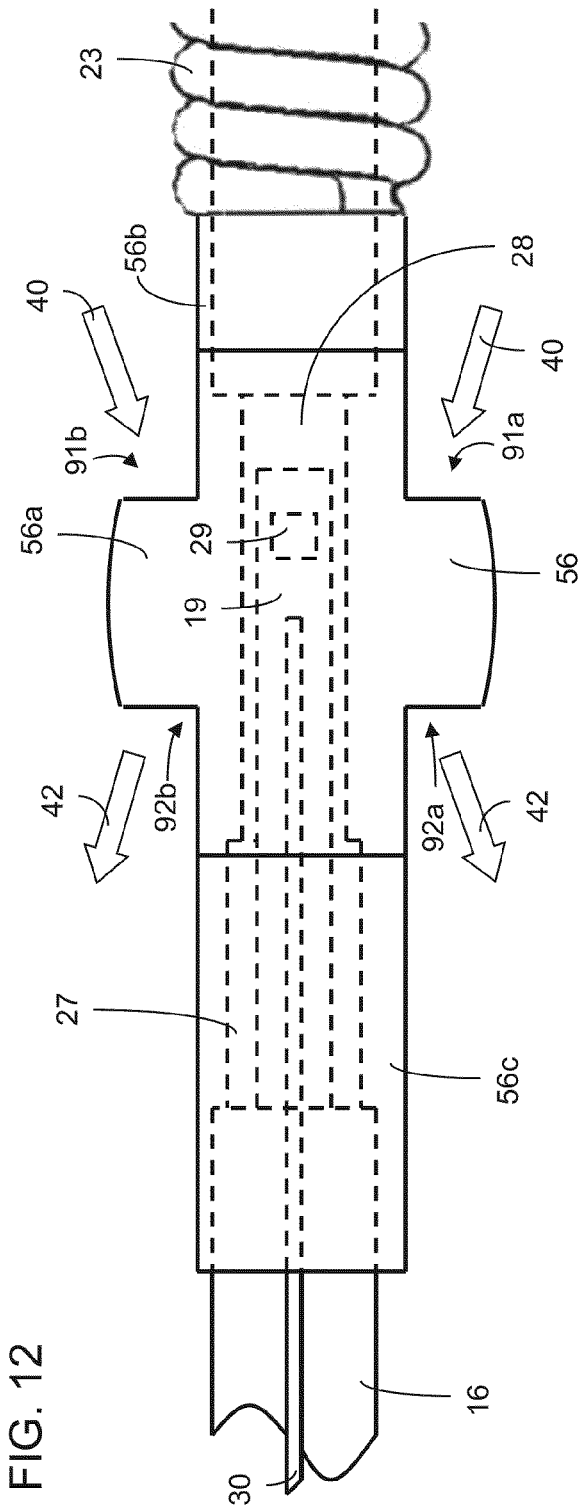

PRESSURE SENSOR AND GUIDE WIRE WITH HYDROPHILIC MATERIAL

CROSS-REFERENCE TO RELATED APPLICATION

This application is a continuation application of U.S. application Ser. No. 15/053,308, filed Feb. 25, 2016, which claims the benefit of U.S. Provisional Application No. 62/121,243, filed on Feb. 26, 2015, the entire contents of all of which are incorporated herein by reference.

BACKGROUND

The present disclosure relates to devices for making pressure or other measurements inside a living body, and in particular to a sensor/guide device having a guide wire and a distal sensor for pressure measurement in stenotic vessels.

Examples of such devices are described, for example, in Swedish Patents SE 441725, SE 453561, SE 454045, SE 460396, and SE 469454, in European Publication EP 0387453, and in U.S. Pat. No. 6,167,763.

U.S. Pat. No. 6,167,763 describes a device in which a pressure sensor is mounted in a cantilevered configuration. In one embodiment, a tube extends around the pressure sensor. An opening is provided in the tube above the pressure sensor to allow the pressure sensor to be exposed to a surrounding medium, the pressure of which is to be measured. While this device has many benefits over previous devices, the present inventors discovered that an unstable pressure column can form above the sensor membrane of the pressure sensor due to insufficient wetting when the device is immersed in a liquid. Without being bound by theory, it is believed that instability in the pressure signal is caused by air remaining in the tube. This air influences the pressure column above the sensor membrane due to time dependent motion as a result of the inverse proportionality between capillary pressure and radius, as shown in the Young-Laplace equation, which describes the capillary pressure difference sustained across the interface between two static fluids due to surface tension.

Thus, there is a need for an improved sensor/guide device having a guide wire and a distal sensor for pressure measurement in stenotic vessels.

All references cited in this disclosure are hereby incorporated by reference in their entireties for the devices, techniques, and methods described therein, and for any disclosure relating to medical sensors and devices.

SUMMARY

In another embodiment, a guide wire for biological pressure measurement includes a tube extending along a longitudinal axis of the guide wire; and a pressure sensor for biological pressure measurement, at least a portion of the pressure sensor being mounted within the tube. The pressure sensor comprises a pressure sensor membrane facing a top side of the tube. The tube includes at least six openings, including: a first distal opening located on a top side of the tube, a second distal opening located on a right side of the tube, offset right of the first distal opening in a circumferential direction, a third distal opening located on a left side of the tube, offset left of the first distal opening in a circumferential direction, a first proximal opening located on a top side of the tube proximal of the first distal opening, a second proximal opening located on a right side of the tube, offset right of the first proximal opening in a circumferential direction, and a third proximal opening located on a left side of the tube, offset left of the first proximal opening in a circumferential direction.

In one aspect, the tube includes exactly six openings: the first, second, and third distal openings, and the first, second, and third proximal openings, such that a bottom of the tube does not include any openings.

In one aspect, the pressure sensor is disposed in the tube such that, in a top view of the guide wire, an entirety of the pressure sensor membrane is visible through the distal opening.

In one aspect, the second and third distal openings are each offset by 90° in opposite circumferential directions from the first distal opening, and the second and third proximal openings are each offset by 90° in opposite circumferential directions from the first proximal opening.

In one aspect, widths of the first distal opening and first proximal opening are greater than widths of the second and third distal openings and second and third proximal openings.

In one aspect, proximal ends of each of the distal openings are at a same longitudinal position of the guide wire, and distal ends of each of the distal openings are at a same longitudinal position of the guide wire, and proximal ends of each of the proximal openings are at a same longitudinal position of the guide wire, and distal ends of each of the proximal openings are at the same longitudinal position of the guide wire.

In one aspect, each of the distal and proximal openings has a generally rectangular shape.

In one aspect, each of the distal and proximal openings has a generally rectangular shape with rounded corners.

In one embodiment, a guide wire for biological pressure measurement comprises a tube extending along a longitudinal axis of the guide wire; and a pressure sensor for biological pressure measurement, at least a portion of the pressure sensor being mounted within the tube. The tube includes at least one concave distal opening extending proximally from a distal edge of the tube.

In one aspect, the at least one concave distal opening is configured to allow a fluid to enter the tube from a region outside the tube via the at least one concave distal opening and flow past the pressure sensor before exiting the tube.

In one aspect, the tube further includes at least one proximal opening located proximal of the at least one concave distal opening.

In one aspect, at least a portion of the at least one concave distal opening is located in a longitudinal cylindrical segment that opposes a side surface of the pressure sensor.

In one aspect, the at least a portion of the at least one concave distal opening is located distal of the pressure sensor.

In one aspect, the tube further includes at least one proximal opening located proximal of the at least one concave distal opening, and at least a portion of the at least one concave distal opening and at least a portion of the at least one proximal opening are located in a longitudinal cylindrical segment that opposes a side surface of the pressure sensor.

In one aspect, the at least one concave distal opening includes at least two concave distal openings.

In one aspect, the at least one concave distal opening includes at least two concave distal openings: a first concave distal opening and a second concave distal opening, and the tube further includes at least two proximal openings: a first proximal opening located proximal of the first concave distal opening, and a second proximal opening located proximal of the second concave distal opening.

In one aspect, the at least one concave distal opening includes at least two concave distal openings: a first concave distal opening and a second concave distal opening, an entirety of the first concave distal opening is located in a first longitudinal half of the tube that opposes a first side of the pressure sensor, and an entirety of the second concave distal opening is located in a second longitudinal half of the tube that opposes a second side of the pressure sensor.

In one aspect, a depth of the at least one concave distal opening is within 10% of a distance between the tube and a side surface of the pressure sensor.

In one aspect, the at least one distal opening has a single rounded edge.

In one aspect, the at least one concave distal opening has at least one straight edge.

In one aspect, the guide wire further comprises a wire on which the pressure sensor is mounted, the wire including a recess over which a distal portion of the pressure sensor extends. The tube further includes at least one proximal opening located proximal of the at least one concave distal opening. The at least one proximal opening is located in a cylindrical section of the tube that is adjacent to a proximal end of the recess.

In one aspect, the guide wire further comprises a wire on which the pressure sensor is mounted, the wire including a recess over which a distal portion of the pressure sensor extends. The pressure sensor is cantilevered from a shelf portion of the wire.

In one aspect, the pressure sensor is an absolute pressure sensor.

In one aspect, the guide wire further comprises a radiopaque tip.

In another embodiment, a guide wire for biological pressure measurement comprises a tube extending along a longitudinal axis of the guide wire; and a pressure sensor for biological pressure measurement, at least a portion of the pressure sensor being mounted within the tube. The tube includes at least one distal opening, and at least one proximal opening located proximal of the at least one distal opening.

In one aspect, the tube includes a first cylindrical section having a first diameter, and a second cylindrical section having a second diameter that is larger than the first diameter, and at least a portion of the at least one distal opening is located at a distal end of the second cylindrical section.

In one aspect, the tube includes a cylindrical section, and a tapered section located at a distal end of the cylindrical section, and at least a portion of the at least one distal opening is located in the tapered section.

In one aspect, the tube includes a first cylindrical section having a first diameter, a second cylindrical section having a second diameter that is larger than the first diameter, and a tapered transition section located between the first cylindrical section and the second cylindrical section, and at least a portion of the at least one distal opening is located in the tapered transition section.

In one aspect, the tube includes an ovoid section, and at least a portion of the at least one distal opening is located at a distal end of the ovoid section.

In one aspect, the tube includes a first cylindrical section having a first diameter, and a second cylindrical section having a second diameter that is larger than the first diameter, at least a portion of the at least one distal opening is located at a distal end of the second cylindrical section, and at least a portion of the at least one proximal opening is located at a proximal end of the second cylindrical section.

In one aspect, the tube includes a cylindrical section, a first tapered section located at a distal end of the cylindrical section, and a second tapered section located at a proximal end of the cylindrical section, at least a portion of the at least one distal opening is located in the first tapered section, and at least a portion of the at least one proximal opening is located in the second tapered section.

In one aspect, the tube includes an ovoid section, at least a portion of the at least one distal opening is located at a distal end of the ovoid section, and at least a portion of the at least one proximal opening is located at a proximal end of the ovoid section.

In one aspect, the at least one distal opening has a single rounded edge.

In one aspect, the at least one distal opening has at least one straight edge.

In one aspect, the guide wire further comprises a wire on which the pressure sensor is mounted, the wire including a recess over which a distal portion of the pressure sensor extends. The at least one proximal opening is located in a cylindrical section of the tube that is adjacent to a proximal end of the recess.

In one aspect, the guide wire further comprises a wire on which the pressure sensor is mounted, the wire including a recess over which a distal portion of the pressure sensor extends. The pressure sensor is cantilevered from a shelf portion of the wire.

In one aspect, the pressure sensor is an absolute pressure sensor.

In one aspect, the guide wire further comprises a radiopaque tip.

In another embodiment, a method comprises providing a guide wire for biological pressure measurement comprising: a tube extending along a longitudinal axis of the guide wire; and a pressure sensor for biological pressure measurement, at least a portion of the pressure sensor being mounted within the tube, wherein the tube includes at least one concave opening extending proximally from a distal edge of the tube; and disposing the guide wire into a vessel of an individual such that a fluid enters the tube from a region outside the tube via the at least one distal opening and flows past the pressure sensor before exiting the tube.

In another embodiment, a method comprises providing a guide wire for biological pressure measurement comprising: a tube extending along a longitudinal axis of the guide wire; and a pressure sensor for biological pressure measurement, at least a portion of the pressure sensor being mounted within the tube, wherein the tube includes at least one first opening, and at least one second opening located proximal of the at least one first opening; and disposing the guide wire into a vessel of an individual such that a fluid enters the tube from a region outside the tube via the at least one first opening and flows past the pressure sensor before exiting the tube via the at least one second opening.

In another embodiment, a guide wire for biological pressure measurement includes a tube extending along a longitudinal axis of the guide wire; and a pressure sensor for biological pressure measurement, at least a portion of the pressure sensor being mounted within the tube. The tube includes at least one distal opening. A hydrophilic material is coated on at least one of an internal surface of the tube, and a surface of the pressure sensor.

In one aspect, the pressure sensor comprises a pressure sensor membrane, and the hydrophilic material is further coated on a surface of the pressure sensor membrane.

In one aspect, the hydrophilic material comprises at least one of polyethylene glycol, polyvinyl alcohol, polyvinylpyrrolidone, carboxymethyl cellulose, hydroxypropyl cellulose, a polysaccharide, and a salt.

In one aspect, the hydrophilic material comprises polyethylene glycol.

In one aspect, the hydrophilic material comprises 20,000 g/mol polyethylene glycol.

In another embodiment, a method includes providing a guide wire for biological pressure measurement comprising: a tube extending along a longitudinal axis of the guide wire; and a pressure sensor for biological pressure measurement, at least a portion of the pressure sensor being mounted within the tube. The tube includes at least one distal opening. A hydrophilic material is coated on at least one of an internal surface of the tube, and a surface of the pressure sensor. The method further includes providing a liquid within the tube, whereby the hydrophilic material dissolves and causes an influx of the liquid into the tube.

In one aspect, the pressure sensor comprises a pressure sensor membrane, and the hydrophilic material is further coated on a surface of the pressure sensor membrane.

In one aspect, the hydrophilic material comprises at least one of polyethylene glycol, polyvinyl alcohol, polyvinylpyrrolidone, carboxymethyl cellulose, hydroxypropyl cellulose, a polysaccharide, and a salt.

In one aspect, the hydrophilic material comprises polyethylene glycol.

In one aspect, the hydrophilic material comprises 20,000 g/mol polyethylene glycol.

BRIEF DESCRIPTION OF THE DRAWINGS

FIG. 9 is a side view of a guide wire according to another exemplary embodiment of the present invention, in which a tube includes a distal tapered section and a proximal tapered section, with internal elements shown in dashed lines.

FIG. 10 is a top view of the guide wire shown in FIG. 9.

FIG. 11 is a side view of a guide wire according to another exemplary embodiment of the present invention, in which a tube includes an ovoid section, with internal elements shown in dashed lines.

FIG. 12 is a top view of the guide wire shown in FIG. 11.

DETAILED DESCRIPTION

Referring generally to the figures, a guide wire used for biological pressure measurements is shown and described. The guide wire may generally include a tube (sometimes termed a "jacket") and pressure sensor. The tube may generally include at least one distal opening, such as a concave distal opening. In various embodiments, the guide wire may include one distal opening and one proximal opening, two concave distal openings and two proximal openings, or otherwise. The use of the concave distal opening may suppress the formation of air pockets in the guide wire surrounding the sensor, thereby permitting a more accurate pressure sensor reading. In other words, the guide wire is "self-wetting" in that the pressure or other sensor is wetted when the guide wire is inserted in a vessel.

Figure 1:
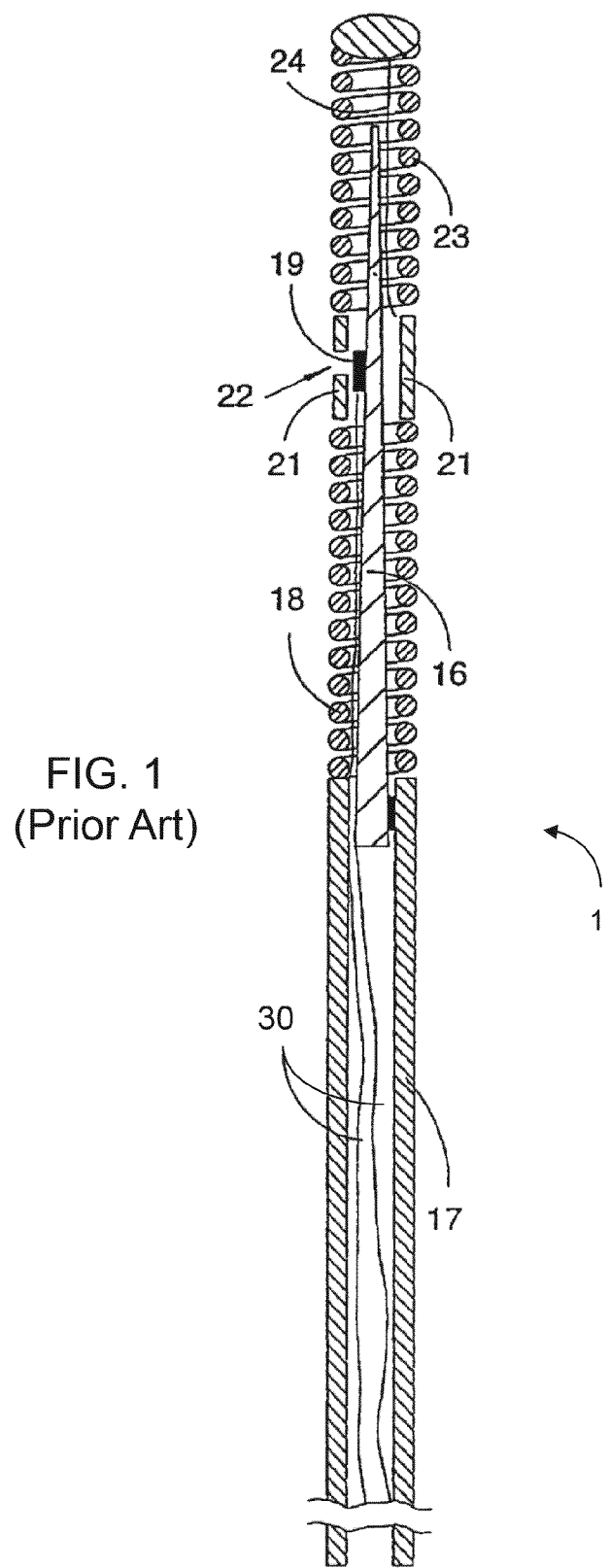
FIG. 1 is a side cross-sectional view of a prior art guide wire including a tube and pressure sensor.

Referring to FIG. 1, a cross section of a prior art guide wire 1 is shown. The guide wire 1 includes a solid wire 16 disposed in a portion of a proximal tubing portion 17. The solid wire 16 may, for example, be machined by centering grinding. The solid wire 16 may form the distal portion of the wire guide 1 and extend beyond the distal end of the proximal tube portion 17, where said proximal tube portion 17 is connected to or integrally formed with a spiral portion 18.

A pressure sensor 19 is mounted on the wire 16. The pressure sensor 19 may be an absolute pressure sensor, such as the one disclosed in Swedish patent application No. 9600334-8. The pressure sensor 19 may include a membrane 29 (shown in FIG. 2) made of, for example, polysilicon and a piezoresistive element. Between the wire 16 and the spiral portion 18, one or more leads 30 may run from the electronic circuitry of the pressure sensor 19. The wire 16, may act as a portion of one of the leads 30, as in FIG. 1.

The membrane 29 of the pressure sensor 19 may be mounted such that bending artifacts are minimized or eliminated (e.g., ensuring that the edges of the chip do not come into contact with the surrounding tube).

The pressure sensor 19 is protected by a short section of a tube 21, having an aperture 22 through which a surrounding medium interacts with the pressure sensor 19. The guide wire 1 further includes, at the very distal end of the guide wire, an X-ray non-transparent spiral 23, made, for example, of platinum, and used for location purposes, and a safety wire 24 for securing the distal part of the spiral 23. In one embodiment, the non-transparent spiral 23 is a radiopaque coil.

In one embodiment, the wire 16 is made of stainless steel. In other embodiments, the wire 16 may be made of a shape memory metal. The proximal tubing 17 and the spiral 18 may be coupled so as to be utilized as an electrical shield.

Figure 2:
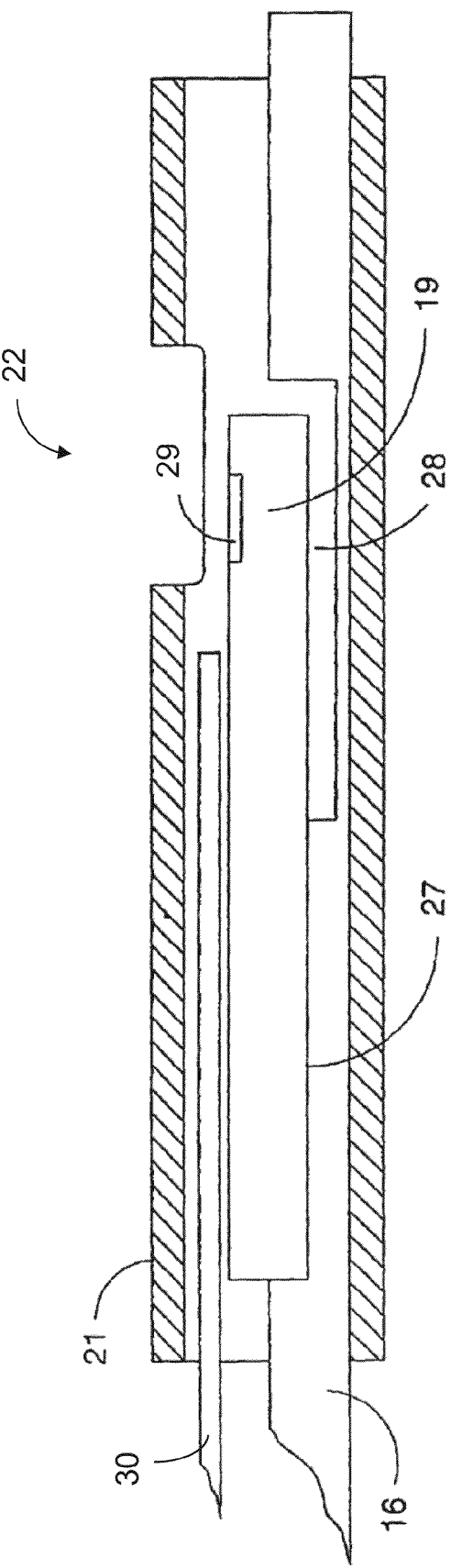
FIG. 2 a side cross-sectional view of a sensor portion of the prior art guide wire shown in FIG. 1.

Referring to FIG. 2, a prior art sensor arrangement of the guide wire 1 is illustrated. The solid wire 16 may be machined (e.g., by grinding, spark erosion, or laser techniques) to form a groove in which the sensor element is mounted in a cantilevering fashion. The groove provides a free space for the sensor 19 and membrane 29, allowing air, blood, or other pressure exerting mediums to enter the interior of the guide wire 1 and act on the sensor, which in turn delivers a signal representative of the exerted pressure.

The groove may consist of two portions. A first portion of the groove may serve as a shelf 27 for receiving the proximal part of the sensor chip and holding the sensor in place. The second portion 28 may be an open space over which the cantilever extends, which allows the distal part of the sensor chip to protrude freely, even in a case where the wire tip is bent or deflected.

As shown in FIGS. 1 and 2, a tube 21 is provided around the guide wire 1, the tube including an opening 22 used to expose the sensor chip to a surrounding medium (e.g., fluid) in order to measure the pressure of the medium.

The prior art embodiments of FIGS. 1 and 2 illustrate a single aperture or opening 22 in the guide wire through which the pressure sensor 19 is exposed to the surrounding medium. However, as discussed above, the presence of air in and around the guide wire 1 may cause unstable sensor readings.

Referring generally to FIGS. 3-12, embodiments of a guide wire according to the present invention will be described. The guide wire generally includes a tube that has at least one distal opening and at least one proximal opening. By implementing embodiments of the present invention, air in the vicinity of the sensor may be displaced when the guide wire is immersed in a liquid, thereby leading to more accurate sensor readings. The distal opening may allow a fluid to enter the tube and flow past the pressure sensor before exiting the tube at the proximal opening (or vice versa).

In each of the embodiments described below, the guide wire may further include a proximal tube portion 17, a spiral portion 18, an X-ray non-transparent spiral 23, leads 30, etc., as generally described with respect to FIG. 1 and discussed in U.S. Pat. No. 6,167,763.

Figure 3:
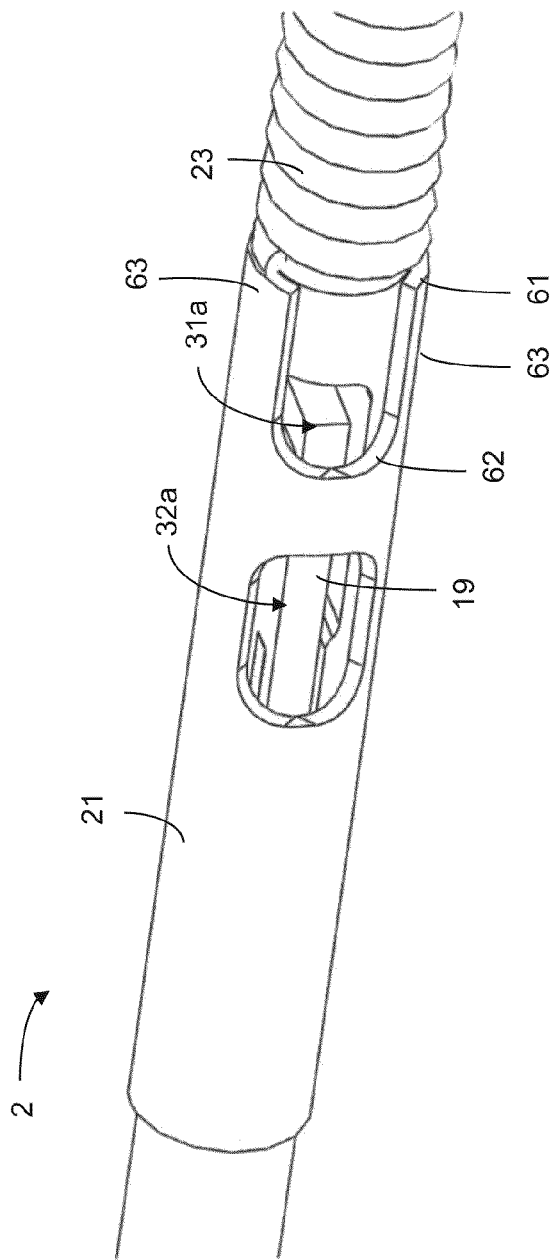
FIG. 3 is a right-side perspective view of a guide wire according to an exemplary embodiment.
Figure 4:
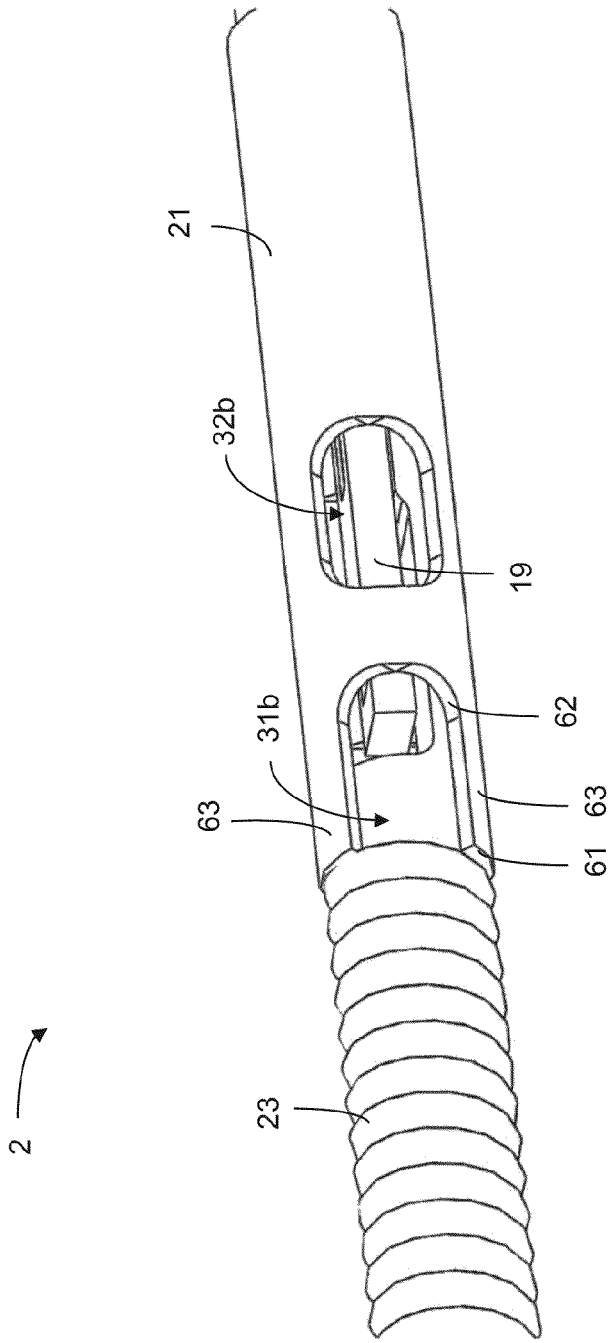
FIG. 4 is a left-side perspective view the guide wire shown in FIG. 3.
Figure 5:
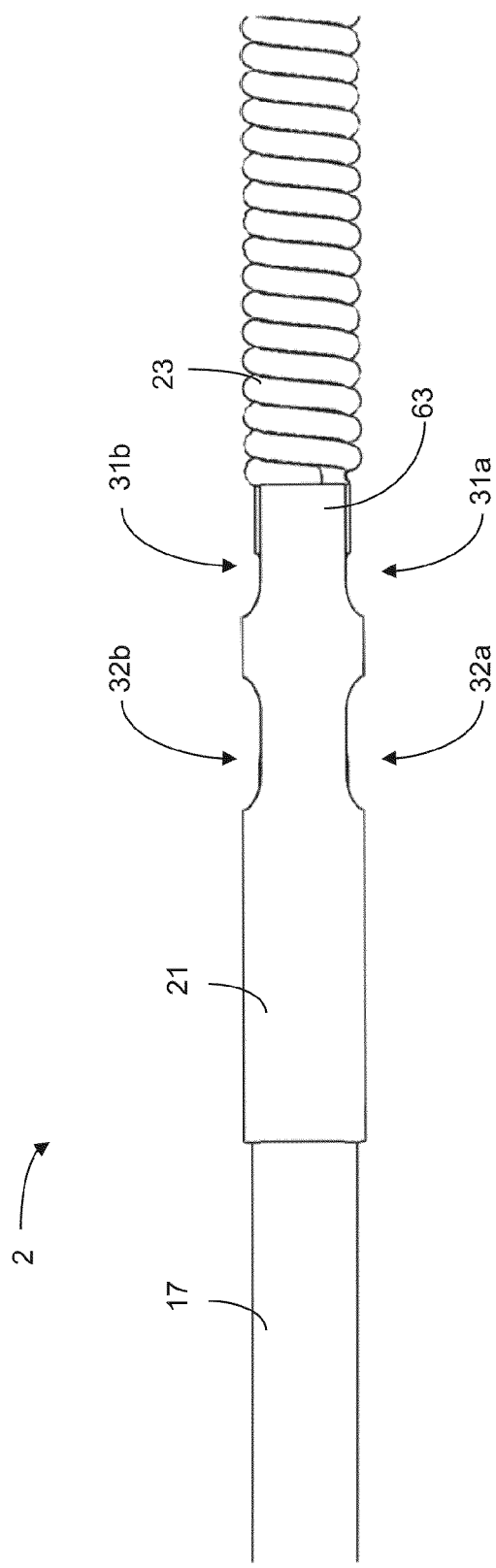
FIG. 5 is a top view of the guide wire shown in FIG. 3.
Figure 6:
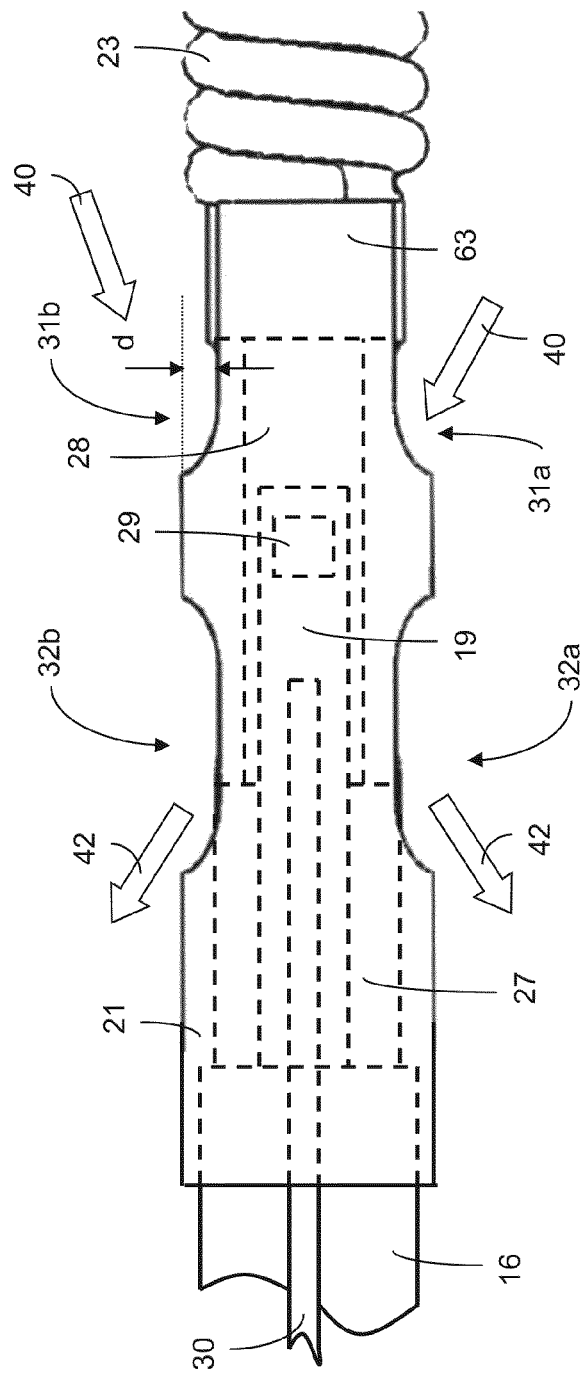
FIG. 6 is a top view of a portion of the guide wire shown in FIG. 3, with internal elements shown in dashed lines.

FIGS. 3-6 depict a guide wire 2 according to a first embodiment. FIG. 3 is a right-side perspective view of a guide wire 2 according to the first embodiment. FIG. 4 is a left-side perspective view the guide wire 2 shown in FIG. 3. FIG. 5 is a top view of the guide wire shown in FIG. 3. FIG. 6 is a top view of a portion of the guide wire shown in FIG. 3, with internal elements shown in dashed lines.

The guide wire 2 includes a tube 21 and pressure sensor apparatus 19.

The tube 21 includes at least one distal opening 31 (for example, two distal openings 31a, 31b as shown in FIG. 5). In the embodiment shown in FIGS. 3-6, the distal opening 31 is a concave distal opening 31 that extends proximally from the distal edge 61 of the tube 21. The term "concave distal opening" as it is used in this disclosure, means that the distal opening 31 is defined by a concave edge 62 of the tube 21. The term "concave" does not imply any particular shape, as long as the concave edge 62 is formed inwardly from the distal edge 61. For example, the concave edge 62 may be rounded, as shown in FIGS. 3-6, or may be formed of multiple straight edges, or a combination of rounded and straight edges. Where the tube 21 includes two of the concave distal openings 31, the concave distal openings 31 separate the distal end of the tube into multiple convex distal sections 63, as shown in FIGS. 3-6. More than two distal openings 31 may be included in the tube 21.

The distal opening 31 may be configured such that a fluid may enter the tube 21 from a region outside of the tube 21 via the distal opening 31 (such that the distal opening 31 is an inlet opening). The fluid may then flow past the pressure sensor 19 before exiting the tube 21 via at least one proximal opening 32, for example, two proximal openings 32a, 32b as shown in FIG. 5, (such that the proximal opening 32 is an outlet opening). The proximal opening 32 may be located proximal of the distal opening 31. In other embodiments, the proximal opening 32 may be an inlet opening and the distal opening 31 may be an outlet opening, depending on the direction in which fluid is flowing relative to the guide wire.

The distal opening 31 and proximal opening 32 are shown located in a longitudinal segment of the tube 21 that opposes a side surface of the pressure sensor 19. The phrase "longitudinal cylindrical segment" refers to a segment of the tube 21 formed by slicing the tube 21 using a longitudinal plane. For example, when the tube 21 includes two distal openings 31a, 31b and two proximal openings 32a, 32b, a first distal opening 31a and a first proximal opening 32a may be located in a first longitudinal half of the tube 21 that opposes a first side of the pressure sensor 19, and a second distal opening 31b and a second proximal opening 32b may be located in a second longitudinal half of the tube 21 that opposes a second side of the pressure sensor 19, as shown in FIGS. 5 and 6. The two distal openings 31a, 31b may be located in a first longitudinal half and second longitudinal half of the tube 21, respectively, such that the openings 31 oppose a first side and second side of the pressure sensor 19.

In the embodiment of FIGS. 3-6, the pressure sensor 19 is shown oriented upwards, and the distal opening 31 and proximal opening 32 are located such that a side of the pressure sensor 19 is exposed. The two distal openings 31 are opposite one another such that the right side of the pressure sensor 19 is exposed in the first distal opening 31a, and the left side of the pressure sensor 19 is exposed in the second distal opening 31b. However, in other embodiments, the entirety of the distal opening 31 may be located distal of the pressure sensor 19 (i.e., when the guide wire is inserted in a vessel, the position of opening 31 is deeper than the position of the pressure sensor 19).

The distal opening 31 is shown with a depth (d) between a major diameter of the tube 21 and a deepest point of the opening 31, when viewed from the side, as shown in FIG. 6. In one embodiment, the depth of the concave distal opening 31 may be approximately equal to a distance between the tube 21 and the side surface of the pressure sensor 19. The term "approximately equal" may be interpreted as, for example, within plus or minus 10%.

Referring to FIG. 6, a top view of the guide wire is illustrated, with internal elements shown in dashed lines. The guide wire includes a tube 21 including two concave distal openings 31a, 31b, and two proximal openings 32a, 32b. The openings 31 and 32 are shown to include a single rounded edge. The pressure sensor 19 is positioned such that fluids may enter the guide wire at the concave distal openings 31a, 31b in a direction 40 and leave at the proximal openings 32a, 32b, in a direction 42, flowing over the pressure sensor 19 along the way. Fluid typically flows in the directions 40, 42 when the guide wire is flushed prior to use. However, when the guide wire is guide wire is inserted into a vessel, blood would typically flow in directions opposite the directions 40, 42 shown in the Figures.

The guide wire further includes a solid wire 16 as described with reference to FIG. 1. The pressure sensor 19 is mounted on the solid wire 16 such that a distal portion of the pressure sensor 19 extends beyond the solid wire 16 into the groove. The solid wire 16 may include a shelf 27 (shown in greater detail in FIGS. 8, 10, and 12) configured to hold the pressure sensor 19 in place, proximal from the two openings 31, 32. The pressure sensor 19 is cantilevered from the shelf portion 27 of the wire (i.e., only one end of the pressure sensor 19 is coupled to the guide wire). A second portion 28 of the groove is shown as an open space around the pressure sensor 19 in which fluids may flow through the guide wire. The proximal openings 32 may be located, for example, near the distal end of the shelf 27 (i.e., the distal portion of the second portion 28 of the groove).

The guide wire is further shown to include an electrical lead 30 running parallel with the pressure sensor 19. The electrical lead 30 may run from the electronic circuitry associated with the guide wire to the guide wire components (e.g., the pressure sensor 19). The wire 16 may act as a portion of a second electrical lead 30.

While the devices shown in the figures include a cantilevered pressure sensor 19, embodiments of the present invention are not limited to include such sensors. Rather, in embodiments of the present invention, the pressure sensor 19 may be any appropriate sensor which can be used to take pressure measurements.

Figure 7:
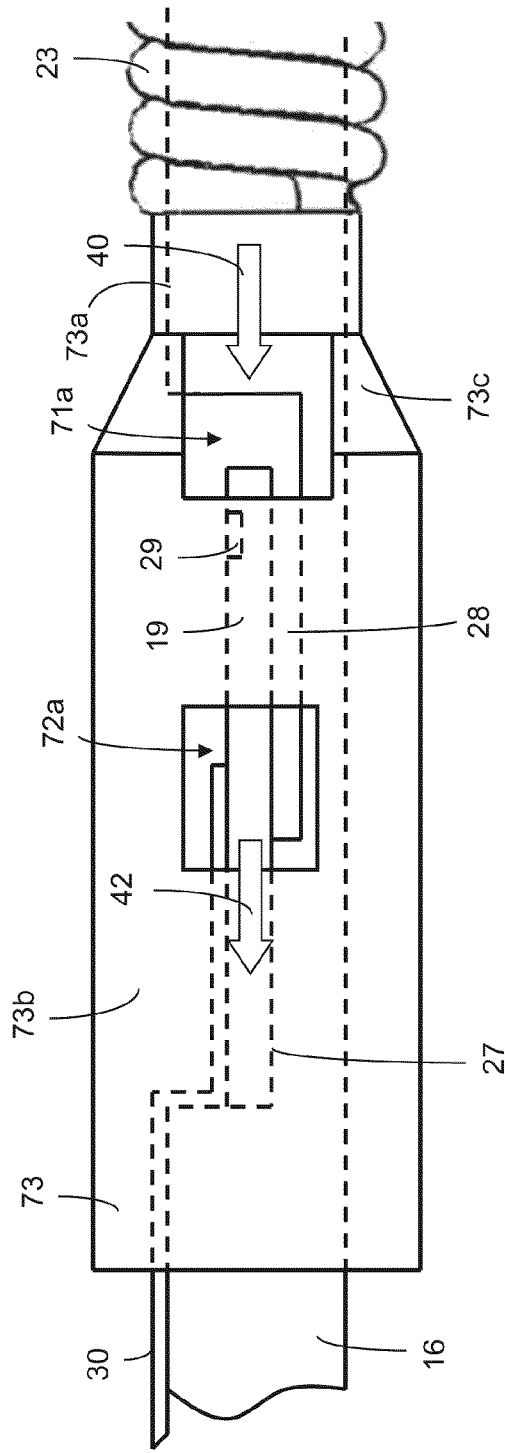
FIG. 7 is a side view of a guide wire according to another exemplary embodiment of the present invention, in which a tube includes a distal tapered section, with internal elements shown in dashed lines.
Figure 8:
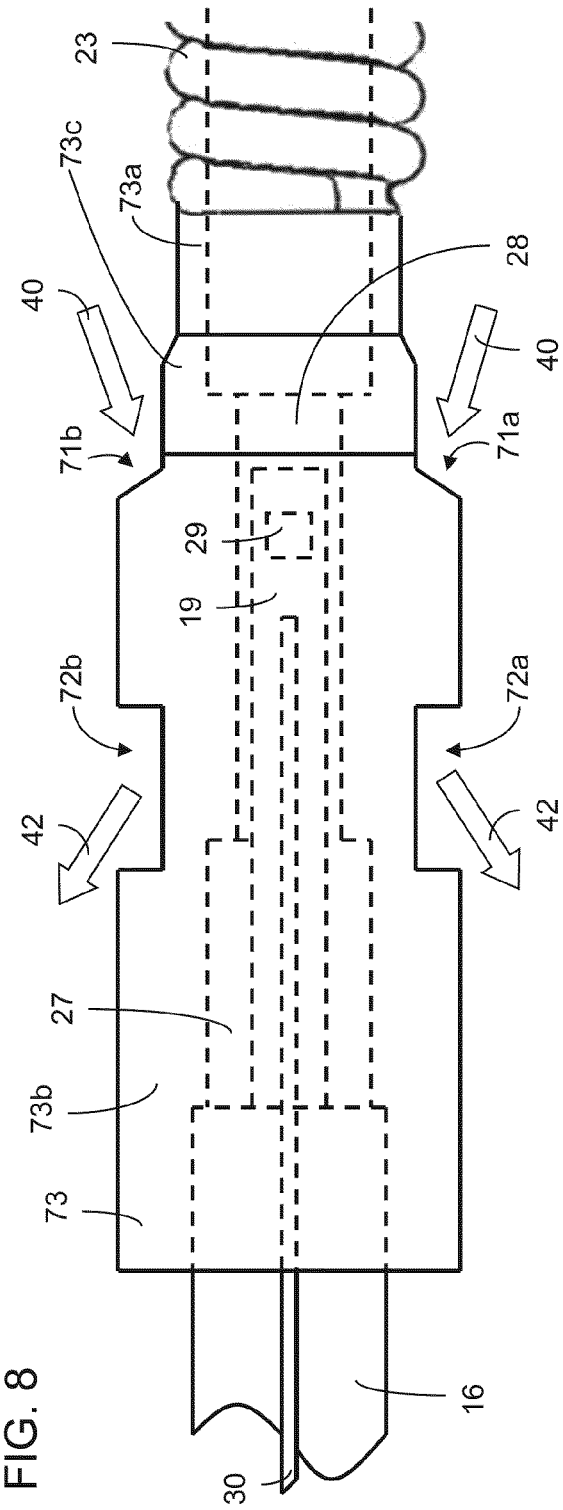
FIG. 8 is a top view of the guide wire shown in FIG. 7.

FIGS. 7 and 8 depict a guide wire according to a second embodiment, in which a tube 73 includes a distal tapered section, with internal elements shown in dashed lines. FIG. 7 is a side view of a guide wire according to the second embodiment. FIG. 8 is a top view of the guide wire shown in FIG. 7.

In the second embodiment, the guide wire includes two distal openings 71a, 71b and two proximal openings 72a, 72b, the distal opening 71a and proximal opening 72a being located opposite the distal opening 71b and proximal opening 72b. The openings 71, 72 are provided such that a side portion of the pressure sensor 19 is exposed in the openings. Each proximal opening 72 is located proximal from its corresponding distal opening 71. The two distal openings 71 may be located in a first longitudinal half and second longitudinal half of the tube 73, respectively, such that the openings 71 oppose a first side and second side of the pressure sensor 19. For example, the two distal openings 71 are opposite one another such that the right side of the pressure sensor 19 is exposed in the first distal opening 71a, and the left side of the pressure sensor 19 is exposed in the second distal opening 71b. In other embodiments, the distal openings 71 and proximal openings 72 may be otherwise positioned, and/or additional openings may be included.

The second embodiment is similar to the first embodiment except, in the second embodiments, the tube 73 includes a first cylindrical section 73a and a second cylindrical section 73b that has a diameter larger than a diameter of the first cylindrical section 73a. The tube 73 further includes a tapered transition section 73c located between the first cylindrical section 73a and the second cylindrical section 73b.

At least a portion of each of the distal openings 71a, and 71b is located at a distal end of the second cylindrical section 73b, as shown in FIGS. 7 and 8. For example, a portion of each of the distal openings 71a, 71b may be formed in the second cylindrical section 73b, and a portion of each of the distal openings 71a, 71b may be formed in the tapered transition section 73c, as shown in FIGS. 7 and 8.

In other embodiments, a portion of each of the distal openings 71a, 71b may also be formed in the first cylindrical section 73a. The distal openings 71a, and 71b may be concave distal openings, as discussed above with respect to FIGS. 3-6. In still other embodiments, the first cylindrical section 73a may be omitted altogether.

As the guide wire is inserted into a vessel, a fluid may flow into the distal openings 71a, 71b in a direction 40, flow over the pressure sensor 19, and flow out of the guide wire through the proximal openings 72a, 72b in a direction 42 (or vice versa).

FIGS. 9 and 10 depict a guide wire according to a third embodiment, in which a tube 52 includes a distal tapered section and proximal tapered section. FIG. 9 is a side view of a guide wire according to the third embodiment, with internal elements shown in dashed lines. FIG. 10 is a top view of the guide wire shown in FIG. 9.

In the third embodiment, the guide wire includes two distal openings 81a, 81b and two proximal openings 82a, 82b, the distal opening 81a and proximal opening 82a being located opposite the distal opening 81b and proximal opening 82b. The openings 81, 82 are provided such that a side portion of the pressure sensor 19 is exposed in the openings. Each proximal opening 82 is located proximal from its corresponding distal opening 81. The two distal openings 81 may be located in a first longitudinal half and second longitudinal half of the tube 52, respectively, such that the openings 81 oppose a first side and second side of the pressure sensor 19. For example, the two distal openings 81 are opposite one another such that the right side of the pressure sensor 19 is exposed in the first distal opening 81a, and the left side of the pressure sensor 19 is exposed in the second distal opening 81b. In other embodiments, the distal openings 81 and proximal openings 82 may be otherwise positioned, and/or additional openings may be included.

The tube 52 of the guide wire in FIGS. 9 and 10 includes a first cylindrical section 52a and a second cylindrical section 52b that has a diameter larger than a diameter of the first cylindrical section 52a. The tube 52 further includes a distal tapered transition section 52c and a proximal tapered transition section 52d, the distal tapered transition section 52c being located distal of the second cylindrical section 52b, and the proximal tapered transition section 52d being located proximal of the second cylindrical section 52b. The tube 52 may further include a third cylindrical section 52e, as shown in FIGS. 9 and 10. Where the tube 52 includes a third cylindrical section 52e, the second cylindrical section 52b may have a diameter that is larger than a diameter of the third cylindrical section 52e.

At least a portion of each of the distal openings 81a, and 81b is located at a distal end of the second cylindrical section 52b. For example, a portion of each of the distal openings 81a, 81b may be formed in the second cylindrical section 52b, and a portion of each of the distal openings 81a, 81b may be formed in the tapered transition section 52c, as shown in FIGS. 9 and 10. At least a portion of each of the proximal openings 82a, 82b is located at a proximal end of the second cylindrical section 52b. For example, a portion of each of the proximal openings 82a, 82b may be formed in the second cylindrical section 52b, and a portion of each of the proximal openings 82a, 82b may be formed in the tapered transition section 52d, as shown in FIGS. 9 and 10.

In other embodiments, a portion of each of the distal openings 81a, 81b may also be formed in the first cylindrical section 52a. The distal openings 81a, and 81b may be concave distal openings, as discussed above with respect to FIGS. 3-6. In still other embodiments, the first cylindrical section 52a may be omitted altogether.

In yet other embodiments, a portion of each of the proximal openings 82a, 82b may also be formed in the third cylindrical section 52e. The proximal openings 82a, 82b may be concave proximal openings, in which case the proximal openings 82a, 82b would be formed similarly to the concave distal openings discussed above with respect to FIGS. 3-6, except that the proximal openings 82a, 82b would extend from a proximal edge of the tube 52, rather than the distal edge. In still other embodiments, the third cylindrical section 52e may be omitted altogether.

As the guide wire is inserted into a vessel, a fluid may flow into the distal openings 81a, 81b in a direction 40, flow over the pressure sensor 19, and flow out of the guide wire through the proximal openings 82a, 82b in a direction 42 (or vice versa).

FIGS. 11 and 12 depict a guide wire according to a fourth embodiment, in which a tube 56 includes an ovoid section. FIG. 11 is a side view of a guide wire according to the fourth embodiment, with internal elements shown in dashed lines. FIG. 12 is a top view of the guide wire shown in FIG. 11.

In the fourth embodiment, the guide wire includes two distal openings 91a, 91b and two proximal openings 92a, 92b, the distal opening 91a and proximal opening 92a being located opposite the distal opening 91b and proximal opening 92b. The openings 91, 92 are provided such that a side portion of the pressure sensor 19 is exposed in the openings. Each proximal opening 92 is located proximal from its corresponding distal opening 91. The two distal openings 91 may be located in a first longitudinal half and second longitudinal half of the tube 56, respectively, such that the openings 91 oppose a first side and second side of the pressure sensor 19. For example, the two distal openings 91 are opposite one another such that the right side of the pressure sensor 19 is exposed in the first distal opening 91a, and the left side of the pressure sensor 19 is exposed in the second distal opening 91b. In other embodiments, the distal openings 91 and proximal openings 92 may be otherwise positioned, and/or additional openings may be included.

The tube 56 of the guide wire in FIGS. 11 and 12 includes an ovoid section 56a. The tube 56 may also include a first cylindrical section 56b located distal of the ovoid section 56a and a second cylindrical section 56c located proximal of the ovoid section 56a, as shown in FIGS. 11 and 12. The maximum diameter of the ovoid section 56a may be larger than the diameters of the first and second cylindrical sections 56b and 56c. The minimum diameter of the ovoid section 56a may be substantially equal to the diameters of the first and second cylindrical sections 56b and 56c.

At least a portion of each of the distal openings 91a, and 91b is located at a distal end of the ovoid section 56a. For example, a portion of each of the distal openings 91a, 91b may be formed in the ovoid section 56a. At least a portion of each of the proximal openings 92a, 92b is located at a proximal end of the ovoid section 56a. For example, a portion of each of the proximal openings 92a, 92b may be formed in the ovoid section 56a.

In other embodiments, a portion of each of the distal openings 91a, 91b may also be formed in the first cylindrical section 56b. The distal openings 91a, and 91b may be concave distal openings, as discussed above with respect to FIGS. 3-6. In still other embodiments, the first cylindrical section 56b may be omitted altogether.

In yet other embodiments, a portion of each of the proximal openings 92a, 92b may also be formed in the second cylindrical section 56c. The proximal openings 92a, 92b may be concave proximal openings, in which case the proximal openings 92a, 92b would be formed similarly to the concave distal openings discussed above with respect to FIGS. 3-6, except that the proximal openings 92a, 92b would extend from a proximal edge of the tube 56, rather than the distal edge. In still other embodiments, the second cylindrical section 56c may be omitted altogether.

Figure 13:
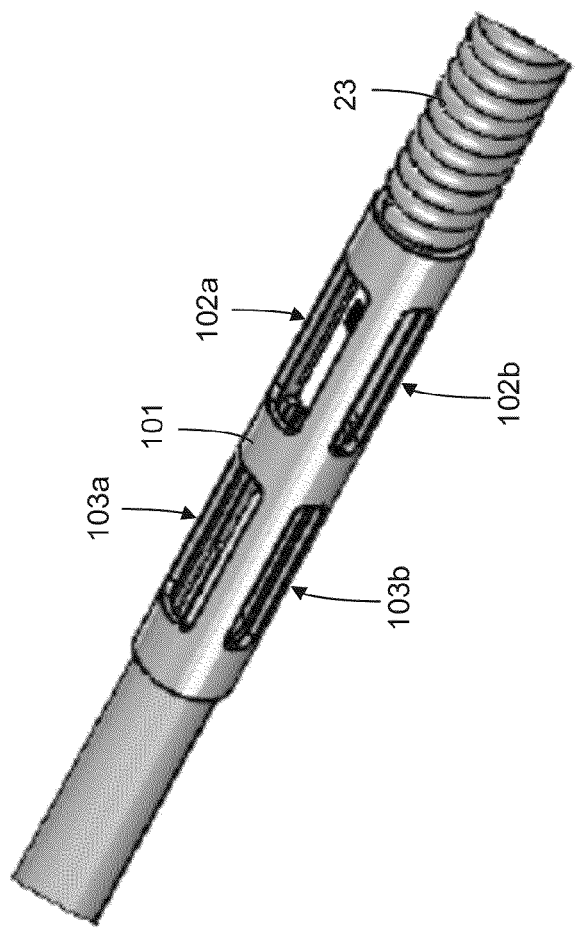
FIG. 13 is a perspective view of the guide wire according to another exemplary embodiment, in which a tube includes six openings.
Figure 14:
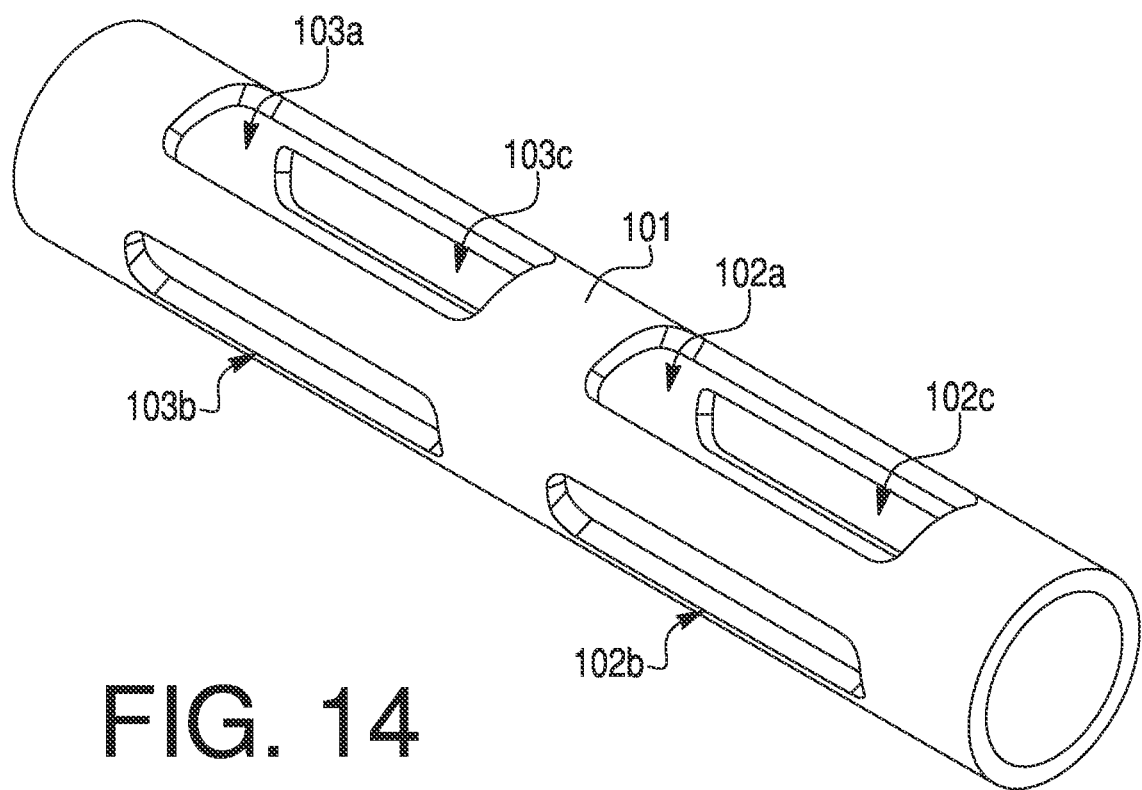
FIG. 14 is a perspective view of the tube of the guide wire shown in FIG. 13.
Figure 15:
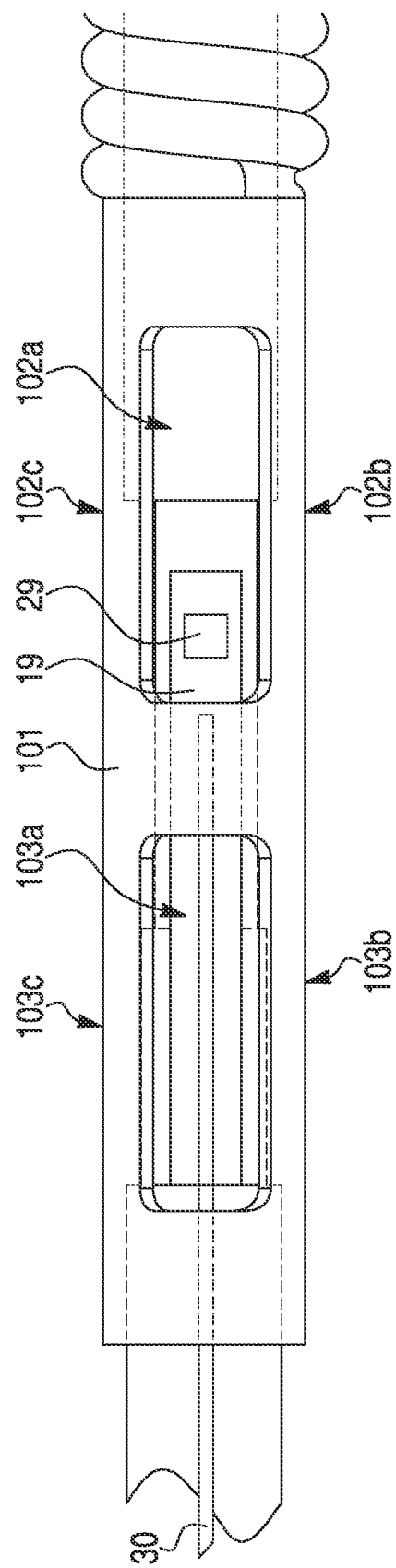
FIG. 15 is a top view of the guide wire shown in FIG. 13
Figure 16:
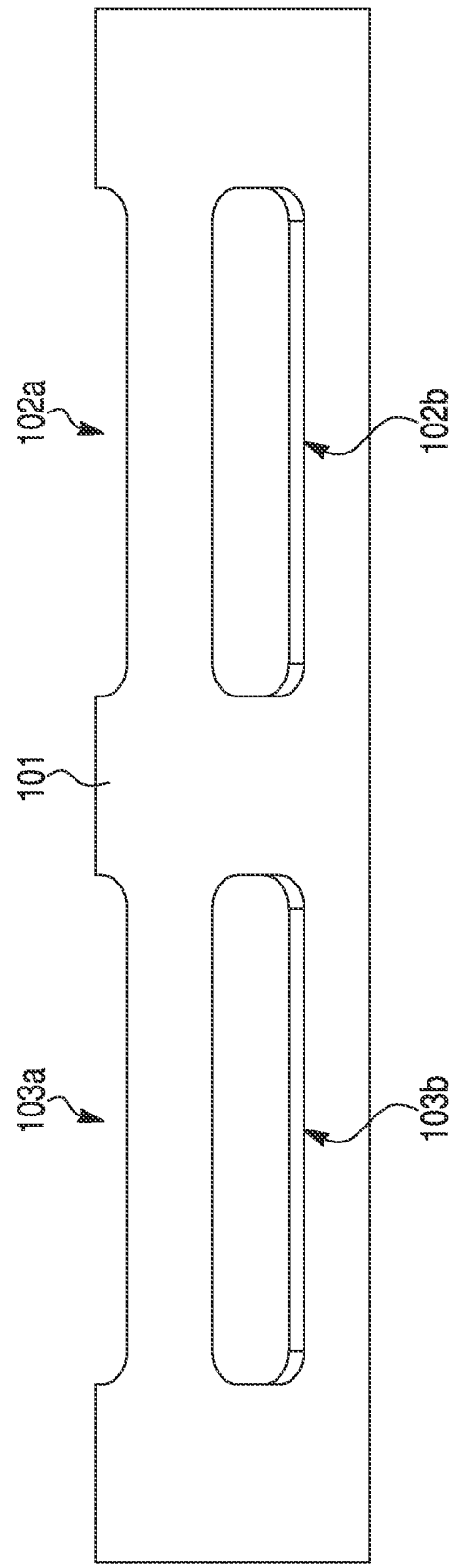
FIG. 16 is a side view of the tube of the guide wire shown in FIG. 13.

FIGS. 13-16 depict a guide wire and a tube 101 thereof according to a fifth embodiment, in which the tube 101 includes six openings 102a, 102b, 102c, 103a, 103b, and 103c in its circumferential wall. FIG. 13 is a perspective view of the guide wire according to the fifth embodiment. FIG. 14 is a perspective view of the tube 101 of the guide wire of the fifth embodiment. FIG. 15 is a top view of the guide wire of the fifth embodiment. FIG. 16 is a side view of the tube 101 of the guide wire of the fifth embodiment. It has been found that the embodiment shown in FIGS. 13-16 yields a particularly effective flow through the tube 101, and largely inhibits formation of air pockets/bubbles in the tube 101 during use.

In the fifth embodiment, the tube 101 of the guide wire includes three distal openings 102a, 102b, 102c and three proximal openings 103a, 103b, 103c. The distal opening 102a and proximal opening 103a are located on a top side of the tube 101, which is a side that is faced by the pressure sensor membrane 29. The distal opening 102b and proximal opening 103b are on a right side of the tube 101. The distal opening 102c and proximal opening 103c are on a left side of the tube 101. The six openings allow for multiple liquid entrance points and multiple air evacuation points, and also aids in the application of a hydrophilic coating to an interior of the tube 101, as discussed in more detail below.

In a preferred embodiment, the tube 101 includes exactly six openings in its circumferential wall, so that a bottom side of the tube 101 does not include any openings. This allows for a core wire to be located at the bottom side of the guide wire without obstructing any of the openings in the circumferential wall of the tube.

The pressure sensor 19 is preferably disposed in the tube 101 such that, in a top view of the guide wire, an entirety of the pressure sensor membrane is visible through the distal opening 102a. The distal openings 102b and 102c are preferably located at the left and right sides of the distal opening 102a. Preferably centers of the distal openings 102b and 102c are each offset by 90° in opposite circumferential directions from a center of the distal opening 102a.

The proximal opening 103a is located proximal of the distal opening 102a. The proximal openings 103b and 103c are preferably located at the left and right sides of the proximal opening 103a. Preferably, centers of the proximal openings 103b and 103c are each offset by 90° in opposite circumferential directions from a center of the proximal opening 103a.

The distal opening 102a is larger than the distal openings 102b, 102c. The proximal opening 103a is larger than the proximal openings 103b, 103c. Preferably, the distal opening 102a and proximal opening 103a have widths that are greater than widths of the distal openings 102b, 102c and proximal openings 103b, 103c, the widths being defined in directions perpendicular to a longitudinal direction of the guide wire. A width of the distal opening 102a and proximal opening 103a may be, for example, in a range of 0.14 to 0.32 mm, preferably 0.17 to 0.29 mm, and more preferably 0.178 to 0.278 mm. A width of the distal openings 102b, 102c and proximal openings 103b, 103c may be, for example, in a range of 0.03 to 0.21 mm, preferably 0.06 to 0.18 mm, and more preferably 0.071 to 0.171 mm.

A distance between the distal opening 102a and the distal openings 102b, 102c may be, for example, in a range of 0.03 to 0.21 mm, preferably 0.06 to 0.18 mm, and more preferably 0.071 to 0.171 mm. A distance between the proximal opening 103a and the proximal openings 103b, 103c may be, for example, in a range of 0.03 to 0.21 mm, preferably 0.06 to 0.18 mm, and more preferably 0.071 to 0.171 mm.

An overall length of the tube 101 may be, for example, in a range of 1.90 to 2.1 mm, and preferably 1.95 to 2.05 mm. A distance from a proximal end of the tube 101 to proximal ends of the proximal openings 103a, 103b, 103c may be, for example, in a range of 0.130 to 0.330 mm, and preferably 0.180 to 0.280 mm. A distance from a proximal end of the tube 101 to the distal ends of the proximal openings 103a, 103b, 103c may be, for example, in a range of 0.785 to 0.985 mm, and preferably 0.835 to 0.935 mm. A distance from a proximal end of the tube 101 to proximal ends of the distal openings 102a, 102b, 102c may be, for example, in a range of 1.015 to 1.215 mm, and preferably 1.065 to 1.165 mm. A distance from a proximal end of the tube 101 to distal ends of the distal openings 102a, 102b, 102c may be, for example, in a range of 1.670 to 1.870 mm, and preferably 1.720 to 1.820 mm.

The proximal ends of each of the distal openings 102a, 102b, 102c are preferably at the same longitudinal position of the guide wire, and the distal ends of each of the distal openings 102a, 102b, 102c are preferably at the same longitudinal position of the guide wire. Similarly, the proximal ends of each of the proximal openings 103a, 103b, 103c are preferably at the same longitudinal position of the guide wire, and the distal ends of each of the proximal openings 103a, 103b, 103c are preferably at the same longitudinal position of the guide wire.

Each of the openings 102a, 102b, 102c, 103a, 103b, 103c has a generally rectangular shape, preferably a rectangular shape with rounded corners.

The overall length of the guide wire may be, for example, between 1.5 m and 2 m, and preferably about 1.75 meters. The tube 21, 52, 56, 73, 101 may have an overall diameter of, for example, between 0.30 and 0.40 mm, and preferably about 0.35 mm. In embodiments that have a reduced diameter tube portion, the diameter of this portion may be, for example, between 0.20 and 0.30 mm, and preferably about 0.25 mm.

In another embodiment, surfaces of the tube and/or pressure sensor (optionally including the pressure sensor membrane) can be treated with a hydrophilic material, to promote influx of liquid (such as water, blood, or saline solution) into the tube to contact the pressure sensor membrane. Coating surfaces of the tube and/or pressure sensor with a hydrophilic material can allow for more stable sensor signals, by reducing air moving through the tube. When submerged in a liquid, the hydrophilic material may dissolve within a few seconds, causing an influx of liquid into the tube and thereby removing air from (or preventing the introduction of air into) the tube.

For example, an inner surface (or "internal circumferential surface") of the tube (such as tubes 21, 52, 56, 73) may be coated with a hydrophilic material. Alternatively or additionally, a surface of the pressure sensor (such as pressure sensor 19) may be coated with a hydrophilic material. Alternatively or additionally, a surface of the pressure sensor membrane (such as pressure sensor membrane 29) may be coated with a hydrophilic material. The jacket may be partially or completely filled with the hydrophilic material. The hydrophilic material may be a material comprising, for example, polyethylene glycol (PEG), polyvinyl alcohol (PVA), polyvinylpyrrolidone (PVP), carboxymethyl cellulose (CMC), hydroxypropyl cellulose (HPC), a polysaccharide, and/or a salt. Preferably, the hydrophilic material is 20,000 g/mol PEG, which has been found to be more stable at elevated aging temperatures than lower molecular weight PEG. Preferably, a PEG dose is in a range of 6 µg to 20 µg. The hydrophilic material comprising PEG may be applied by, for example, by dispensing or vacuum filling a mixture of 3%-10% PEG (preferably 5% PEG) dissolved in 90%-97% ethanol (preferably 95% ethanol) inside the tube. A PEG application of 0.2 µL of a 5% PEG solution (which will yield a PEG dose in the desired range of 6 µg to 20 µg) is preferred. The mixture can be dried using, for example, a heat lamp, so that the ethanol evaporates, leaving a PEG coating on an interior of the tube and/or on the sensor membrane. The application of a hydrophilic material to the interior of the six-opening tube 101 of the fifth embodiment, described above, has been found to be particularly effective in terms of preventing air from accumulating in the tube 101.

It should be understood that even more variations of tube shapes and opening alignments are possible. For example, the tubes may include any number of cylindrical sections of different diameters, and may include any number of tapered sections or other sections to transition between the cylindrical sections. The sections of the tubes may be of any shape (e.g., rectangular, ovoid, spherical, etc.). The distal openings and proximal openings may be located in any of the sections of the tube such that fluids flow into the guide wire at a distal end of the guide wire though the distal openings, and flows over the pressure sensor 19 and through the proximal openings (or vice versa).

The invention being thus described, it will be clear that the same may be varied in many ways. Such variations are not to be regarded as a departure from the spirit and scope of the invention and all such modifications as would be clear to one skilled in the art are intended to be included within the scope of the following claims.

What is claimed is:

1. A sensor wire for biological pressure measurement comprising:
   an elongated member; and
   a pressure sensor configured for biological pressure measurement, the pressure sensor being mounted at a distal end portion of the elongated member,
   wherein a hydrophilic material is coated on a surface of the pressure sensor, the hydrophilic material being dissolvable in blood and dissolvable in saline solution.

2. The sensor wire of claim 1, wherein the pressure sensor comprises a pressure sensor membrane, and the hydrophilic material is coated on a surface of the pressure sensor membrane.

3. The sensor wire of claim 2, wherein the hydrophilic material comprises at least one of polyethylene glycol, polyvinyl alcohol, polyvinylpyrrolidone, carboxymethyl cellulose, hydroxypropyl cellulose, a polysaccharide, and/or a salt.

4. The sensor wire of claim 2, wherein the hydrophilic material comprises polyethylene glycol.

5. The sensor wire of claim 2, wherein the hydrophilic material comprises 20,000 g/mol polyethylene glycol.

6. The sensor wire of claim 1, wherein the hydrophilic material comprises at least one of polyethylene glycol, polyvinyl alcohol, polyvinylpyrrolidone, carboxymethyl cellulose, hydroxypropyl cellulose, a polysaccharide, and/or a salt.

7. The sensor wire of claim 1, wherein the hydrophilic material comprises polyethylene glycol.

8. The sensor wire of claim 1, wherein the hydrophilic material comprises 20,000 g/mol polyethylene glycol.

* * * * *